United States Patent [19]

Mayol

[11] Patent Number: 6,150,365

[45] Date of Patent: Nov. 21, 2000

[54] ANXIETY METHOD

[75] Inventor: Robert F. Mayol, Durham, Conn.

[73] Assignee: Bristol-Myers Squibb Company, Princeton, N.J.

[21] Appl. No.: 09/588,221

[22] Filed: Jun. 6, 2000

Related U.S. Application Data

[60] Continuation-in-part of application No. 09/484,161, Jan. 18, 2000, abandoned, which is a division of application No. 09/368,842, Aug. 5, 1999, abandoned.

[51] Int. Cl.$^7$ .............................................. A61K 31/505
[52] U.S. Cl. ........................................................ 514/252.15
[58] Field of Search ......................................... 514/252.15

[56] References Cited

U.S. PATENT DOCUMENTS

| | | | |
|---|---|---|---|
| 3,717,634 | 2/1973 | Wu et al. | 260/256 YN |
| 4,182,763 | 1/1980 | Casten et al. | 424/251 |
| 4,409,223 | 10/1983 | Riblet et al. | 424/251 |
| 5,431,922 | 7/1995 | Nicklasson | 424/490 |
| 5,633,009 | 5/1997 | Kenealy et al. | 424/448 |
| 6,008,222 | 12/1999 | Salazar | 514/255 |

OTHER PUBLICATIONS

Kerns, et al., "Buspirone Metabolite Structure Profile Using a Standard Liquid Chromatographic–Mass Spectrometric Protocol," *J. Chromatography B*, 698, 1997, pp. 133–145.

Goldthwaite, et al., "Liquid Chromatography/Chemical Reaction Interface Mass Spectrometry as an Alternate to Radioisotopes for Quantitative Drug Metabolism Studies," *Anal. Chem.*, 68/17, 1996, pp. 2996–3001.

Jajoo, et al., "Metabolism of the Antianxiety Drug Buspirone in the Rat," *Drug Metabol. And Disp.*, 17/6, 1989, pp. 625–633.

Jajoo, et al., Metabolism of the Antianxiety Drug Buspirone in Human Subjects, *Drug Metab. and Disposition*, 17/6, pp. 634–640, 1989, 6–Hydroxy Buspirone.

Mayol, et al., "Pharmacokinetics and Disposition of $^{14}$C–Buspirone HC1 After Intravenous and Oral Dosing in Man," *Clin. Pharmacol. Ther.*, 37, p. 210, 1985.

Gammans, et al., "Metabolism and disposition of Buspirone," *American J. Med.*, 80, Suppl. 3B, p. 41–51, 1986, is referenced on p. 1, line 23.

Vandermaelen, et al., "Inhibition of Serotonergic Dorsal Raphe Neurons by Systemic and Iontophoretic Administration of Buspirone, A Non–Benzodiazepine Anxiolytic Drug," *Eur. J. Pharmacol.*, 129 (1–2), pp. 123–130, 1986, 5–Hydroxybuspirone.

Garattini, et al., "Notes on Buspirone's Mechanisms of Action," *J. Clin. Psychiatry*, 43, sec. 2, pp. 19–22, 1982.

Caccia, et al., "1–(2–Pyrimidinyl)–Piperazine as Active Metabolite of Buspirone in Man and Rat," *Pharmacology*, 33, pp. 46–51, 1986.

Cervo, et al., "Different Effects of Intracerebral and Systemic Administraiton of Buspirone in the Forced Swimming Test: Involvement of a Metabolite," *Life Sciences*, 43, pp. 2095–2102, 1988.

Martin, "1–(2–Pyrimidinyl–piperazine May Alter the Effects of the 5–HT1A Agonists in the Learned Helplessness Paradigm in Rats," *Psychopharmacology*, 104, pp. 275–278, 1991.

Jajoo, et al., "In Vitro Metabolism of the Antianxiety Drug Buspirone as a Predictor of Its Metabolism In Vivo," *Xenobiotica*, 20/8, pp. 779–786, 1990, 6–Hydroxy Buspirone.

*Primary Examiner*—Shep K. Rose
*Attorney, Agent, or Firm*—Richard P. Ryan

[57] ABSTRACT

6-Hydroxy-8-[4-[4-(2-pyrimidinyl)-piperazinyl]-butyl]-8-azaspiro[4.5]-7,9-dione and its pharmaceutically acceptable salts and hydrates are useful in the alleviation of anxiety.

1 Claim, 5 Drawing Sheets

ANXIETY METHOD

CROSS REFERENCE TO RELATED APPLICATIONS

This application is a continuation-in-part of application Ser. No. 09/484,161 filed Jan. 18, 2000, now abandoned which is a divisional application of application Ser. No. 09/368,842 filed Aug. 5, 1999 now abandoned.

BACKGROUND OF THE INVENTION

The present invention involves an improved process for the alleviation of anxiety by treatment with an anxiolytically effective amount of 6-hydroxy-8-[4-[4-(2-pyrimidinyl)-piperazinyl]-butyl]-8-azaspiro[4.5]-7,9-dione. This compound was first disclosed by Jajoo, et al., *Drug Metab. and Disposition*, 17/6, pp. 634–640, 1989, as being one of several metabolites of the clinically useful anxiolytic drug, buspirone. Confirmation of structure for this metabolite was achieved by comparison with an authentic sample of the compound prepared synthetically. This metabolite compound has been designated BMY 28674, and is also known as BMY 28674.

The parent drug, buspirone, has the following chemical structure.

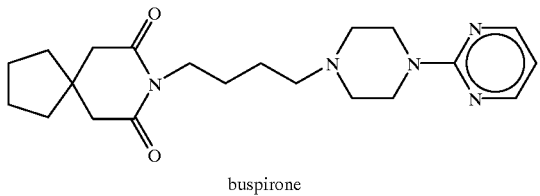

buspirone

Buspirone, chemically: 8-[4-[4-(2-pyrimidinyl)1-piperazinyl]butyl-8-azaspiro(4,5)-decane-7,9-dione, is a pharmaceutically active compound which has been found to be effective for the treatment of anxiety disorders and depression. It is accepted that buspirone exerts its effects through the serotonin 1A (5-HT1A) receptor. However, buspirone shows a very high first pass metabolism and, in general, only about 4% of a therapeutic dose of buspirone reaches the systemic circulation in non-metabolized form after oral administration (Mayol, et al., *Clin. Pharmacol. Ther.*, 37, p. 210, 1985). Large differences in buspirone absorption between individuals have also been observed. This has been demonstrated by variations of the maximum plasma concentration of drug in individuals by up to 10-fold differences (Gammans, et al., *American J. Med.*, 80, Suppl. 3B, pp. 41–51, 1986).

Synthesis of buspirone and related analogs and disclosure of their psychotropic properties are described by Wu, et al., in U.S. Pat. No. 3,717,634. The use of buspirone hydrochloride as a novel antianxiety agent for the treatment of neurotic patients is described by Casten, et al., in U.S. Pat. No. 4,182,763.

BMY 28674 was previously tested for antianxiety properties using laboratory methods specifically developed for the measurement of antianxiety properties in azapirone compounds such as buspirone, gepirone and structural analogs. No significant antianxiety activity was ever detected for BMY 28674 in this testing. No significant biological activity of any type has ever been disclosed for this compound. Indeed, with the exception of 1-pyrimidinylpiperazine (1-PP), no significant antianxiety activity has been disclosed for any of the known buspirone metabolites. See: Gammans, et al., *JAMA*, (March, 1986), Vol. 80, Supp. 3B, pp. 43–44. As a consequence, oral dosing of buspirone for treating anxiety has been believed to be optimized when done in a manner to maximize the concentration of unchanged drug at the expense of metabolites.

In U.S. Pat. No. 5,431,922 an extended-release formulation of buspirone was described as providing an improvement in oral administration of the drug on the basis that blood levels of unchanged buspirone were increased while metabolite levels were reduced as measured by the ratio of plasma levels of buspirone to the 1-PP metabolite. However, no efficacy data were ever disclosed for these formulations nor were they commercialized.

U.S. Pat. No. 5,633,009 disclosed and claimed a transdermal patch for delivering buspirone. The transdermal delivery, as expected, reliably gave higher buspirone blood levels (AUC) with much reduced metabolite levels, as measured by 1-PP. A typical patch was designed to deliver 60 mg of buspirone per 24 hour period. Surprisingly, clinical studies conducted with this patch demonstrated an anxiolytic effect that was not distinguishable from placebo.

Most recently an improved method for oral administration of buspirone was claimed in U.S. Pat. No. 6,008,222 wherein the bioavailability of unchanged buspirone is increased and metabolite formation is decreased. The disclosed method involved co-administration of buspirone with the drug nefazodone, an inhibitor of cytochrome P4503A4 (CYP3A4). Based on assessment of preliminary clinical data, no further development of this drug combination pharmaceutical formulation has been planned.

In summary, while BMY 28674 has been found to be one of several human metabolites resulting from oral administration of the anxiolytic drug, buspirone, no useful biological activity has previously been associated with the compound itself prior to the present invention. In particular, no anxiolytic activity was detected in previous testing. Dosing recommendations for buspirone have been made in accordance with the expectation that inhibition of buspirone's metabolism would generate a more robust antianxiety response. The clinical observation that a certain percentage of anxious patients do not get relief from administration of buspirone has been ascribed to insufficient levels of parent drug being achieved in these non-responders. A second clinical observation regarding a seven to ten day lag period prior to observation of an anxiolytic effect has been attributed to a requirement for a change in receptor site dynamics as a result of chronic buspirone administration. The unexpected discovery of the anxiolytic effects of BMY 28674 suggests other explanations for these observations.

SUMMARY AND DETAILED DESCRIPTION OF THE INVENTION

Figure 1:
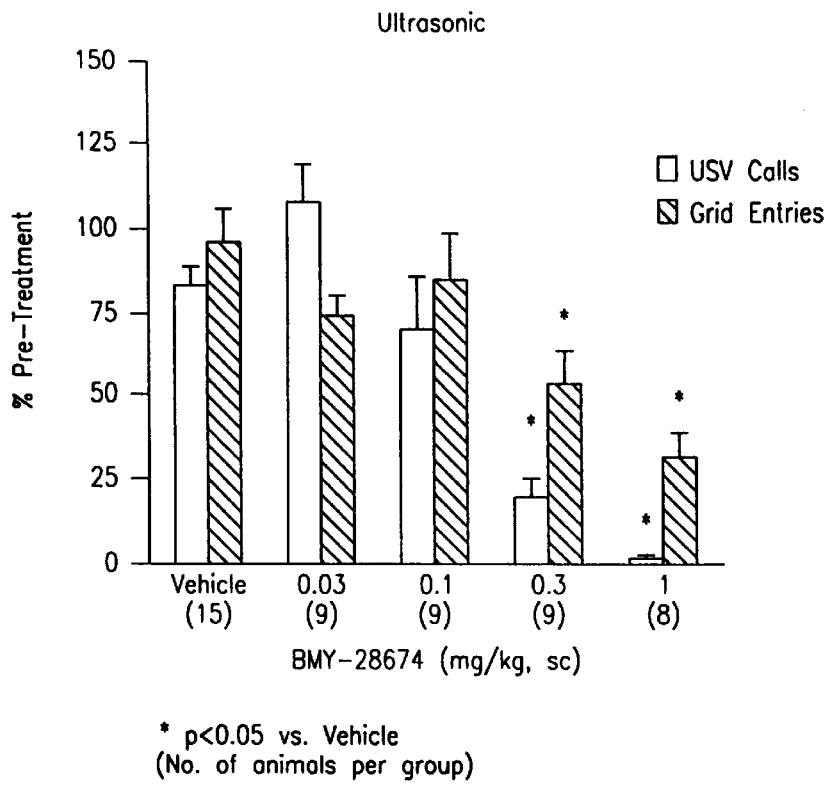
FIG. 1. Effect of BMY 28674 on isolation-induced ultrasonic vocalization and locomotor activity in the rat pup.

We have discovered that 6-hydroxy-8-[4-[4-(2-pyrimidinyl)-piperazinyl]-butyl]-8-azaspiro[4.5]-7,9-dione (I) is useful as an agent to treat anxiety and is referred to herein as BMY 28674. The compound has the following structural formula:

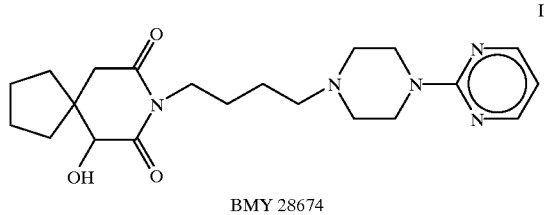

BMY 28674 and is believed to be the active metabolite of buspirone.

As a result of previous in-house testing of the clinically useful anxiolytic agent buspirone, and several of its putative and actual metabolites, the prevailing view has been that the anxiolytic action was mainly provided by buspirone itself with little, if any, contribution being made by buspirone metabolites. For example, systemic administration (I.V. and intragastric) of certain putative metabolites to rats resulted in little to no inhibition of dorsal raphe neuronal firing. In contrast, buspirone itself potently inhibits the firing of dorsal raphe neurons. See: VanderMaelen, et al., *Eur. J. Pharmacol.*, 129, pp. 123–30, 1986. While one metabolite, the structural fragment 1-(2-pyrimidinyl)piperazine, also known as 1-PP,

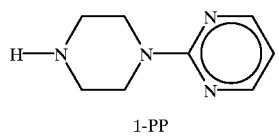

1-PP did show weak inhibition of dorsal raphe firing as well as eliciting some antianxiety activity in certain other preclinical tests (see: U.S. Pat. No. 4,409,223), it also displayed anxiogenic properties in other behavioral testing paradigms. See: Cervo, et al., *Life Sciences*, 43, pp. 2095–2102, 1988; Martin, *Psychopharmacology*, 104, pp. 275–278, 1991. It is probable that the biological effect of 1-PP is mediated through an alpha 2 adrenergic mechanism as 1-PP does not demonstrate binding at the 5-HT1A receptor. Presently, the clinical effect of 1-PP is unclear.

With general acceptance that the active anxiolytic agent is buspirone itself, dosing instructions are currently provided in accordance with maximizing blood levels of unchanged buspirone in anxious patients. In patients where metabolism of buspirone is inhibited, either because of the patient's hepatic enzymatic activity levels or because of ingestion of substances that have inhibitory effects on hepatic metabolism, particularly CYP3A4; patients are being advised to reduce the amount of buspirone being taken. It is interesting that no specific correlation of adverse effects with higher buspirone blood levels has been established. With discovery of the instant active metabolite, the direction of such dosing instructions should be changed to conditions favoring enzymatic production of BMY 28674. In effect, the dose of buspirone should be increased, not decreased, in patients characterized by inhibited buspirone metabolism.

Another widely accepted hypothesis deals with buspirone not providing relief from anxiety in a certain percentage of patients. This lack of effect has been ascribed to insufficient blood levels of unchanged buspirone being achieved in non-responders even though buspirone blood levels are very low in all patients. Scientific confirmation of this explanation for treatment failure is lacking. An alternate explanation emerges in light of the discovery of the active metabolite BMY 28674 and its anxiolytic effect. A more likely explanation for treatment failure in certain patients concerns the relationship of anxiolytic efficacy to blood levels of BMY 28674. Non-responders are seen as those patients whose metabolic conversion of buspirone to BMY 28674 is insufficient to achieve efficacious levels of BMY 28674. Relating to this explanation is the observation of the wide variability of buspirone blood levels seen both within the same patient and between patients following oral administration. This variability can be a result of known variations that occur in activity levels of human hepatic metabolism during the course of daily living. However, since blood levels of buspirone itself are very low, the differences in buspirone blood levels are generally small in comparison to the differences in blood levels seen for the more abundant metabolites.

Similarly, the time lag observed for onset of anxiolytic action following initiation of buspirone treatment can involve the time required for metabolite accumulation as well as re-regulation of receptor site dynamics. In general, the dependence of anxiolytic action on appearance of the metabolite BMY 28674 correlates well with clinical observations made with respect to oral administration of buspirone to anxious patients.

On the basis of the accepted rationale that intact buspirone provided the useful antianxiety activity seen clinically, a transdermal patch delivery system for buspirone was developed (see: U.S. Pat. No. 5,633,009). A buspirone transdermal patch was predicted to be a superior treatment for anxiety since transdermal drug delivery resulted in minimized metabolism of buspirone, thereby giving significantly larger amounts of parent drug with much reduced levels of metabolites. Surprisingly, little to no anxiolytic activity was seen clinically with use of the buspirone transdermal patch. This unexpected result has led to reevaluation of buspirone metabolites and the discovery of BMY 28674's potent antianxiety action.

The following metabolic scheme (Scheme 1) for buspirone is taken from Jajoo, et al., *Xenobiotica*, 1990, Vol. 20, No. 8, pp. 779–786, "In vitro metabolism of the antianxiety drug buspirone as a predictor of its metabolism in vivo."

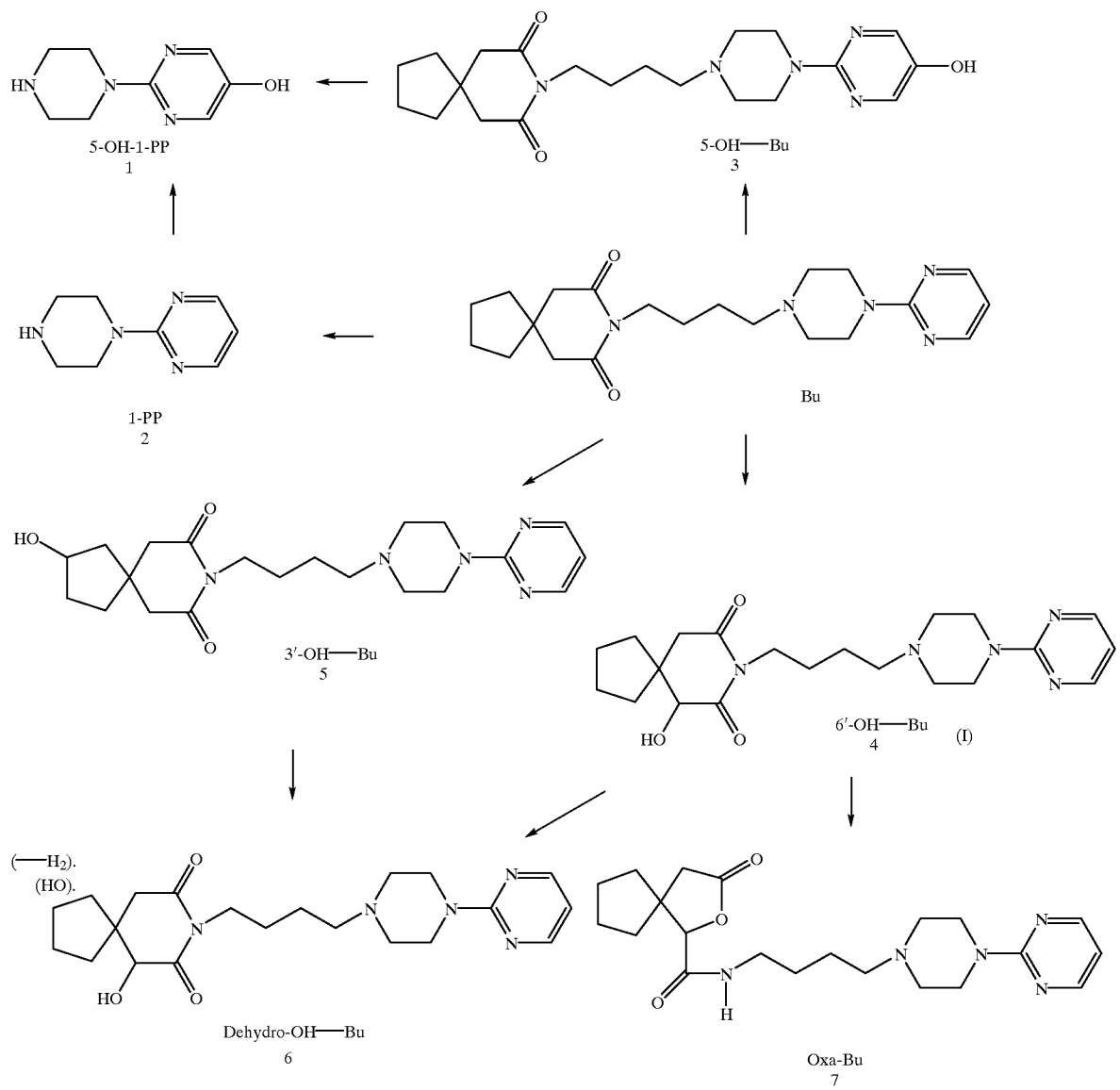

Scheme 1
Scheme for metabolism of buspirone by rat liver microsomes and hepatocytes The new work began by evaluation of relevant receptor binding of buspirone metabolites. Accordingly, the in vitro activity of buspirone (Bu; MJ 9022) and its metabolites 1-PP (BMY 13653), 3'-OH-buspirone (BMY 14295), 5-OH-buspirone (BMY 14131), and 6'-OH-buspirone (BMY 28674); were evaluated for activity at the human 5-HT1A receptor. Results of these experiments are found in Table 1.

TABLE 1

| Compound | $IC_{50}$ [nM] | STDEV | $K_i$ value | N |
| --- | --- | --- | --- | --- |
| 8-OH-DPAT (reference) | 2.5 | 0.9 | 1 | 8 |
| Buspirone (MJ 9022) | 30 | 18 | 15 | 8 |
| 6-OH-buspirone (BMY 28674) | 114 | 85 | 57 | 7 |
| 5-OH-buspirone (BMY 14131) | 928 | 176 | 464 | 7 |

TABLE 1-continued

| Compound | $IC_{50}$ [nM] | STDEV | $K_i$ value | N |
| --- | --- | --- | --- | --- |
| 3-OH-buspirone (BMY 14295) | 652 | 402 | 326 | 7 |
| 1-PP (BMY 13653) | >1000 | — | — | 3 |

As can be seen, Table 1 summarizes the new in vitro action of MJ 9022 (buspirone) and its metabolites BMY 13653 (1-PP), BMY 14131 (5-OH-buspirone), BMY 14295 (3-OH-buspirone), and BMY 28674 (6-OH-buspirone) at the human serotonin 1A (5-HT1A) receptor. Buspirone demonstrates a high affinity for the human 5-HT1A receptor ($K_i$=15 nM). BMY 28674 has a binding affinity that approaches that of buspirone ($K_i$=57 nM). The other metabolites tested have relatively weak affinity for human 5-HT1A receptor compared to buspirone.

BMY 28674 appears to be the active metabolite of buspirone. Not only is it the second most abundant metabolite obtained in the metabolism studies from human urine (5-hydroxy-1PP being most

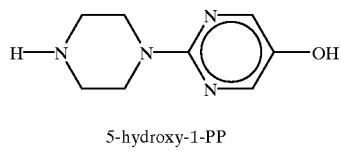

5-hydroxy-1-PP abundant); but more importantly, human blood levels of BMY 28674 are about 40 times greater than those of buspirone and several-fold greater than those of 1-PP. Also of significance is the fact that the skeletal structure of buspirone remains intact in BMY 28674. In addition, binding data at the 5-HT1A receptor indicates that BMY 28674 has a binding affinity closer to that of buspirone in contrast to other metabolites which demonstrate only weaker interaction at the 5-HT1A site. The 5-HT1A receptor is currently accepted as the serotonergic receptor intimately involved in regulation of anxiety. The present research focus has been on buspirone metabolites that maintain the buspirone skeletal structure and that have no more than one hydrophilic hydroxy group incorporated into the molecule. The presence of more than one hydrophilic hydroxy group is likely to reduce the distribution and transport of those polyhydroxylated metabolic products into the CNS regions of the body thereby making requisite receptor interactions unlikely to occur in target regions.

Earlier in-house functional testing of BMY 28674 utilized an in vivo test method based on modification of the Vogel Conflict test, a simple reliable conflict procedure for testing antianxiety agents (see: Vogel, et al., *Psychopharmacologia*, (Berl.) 21, pp. 1–7, 1971). However, BMY 28674 did not elicit an antianxiety response in the Vogel test. No useful antianxiety activity has been ascribed to BMY 28674 previously.

Figure 2:
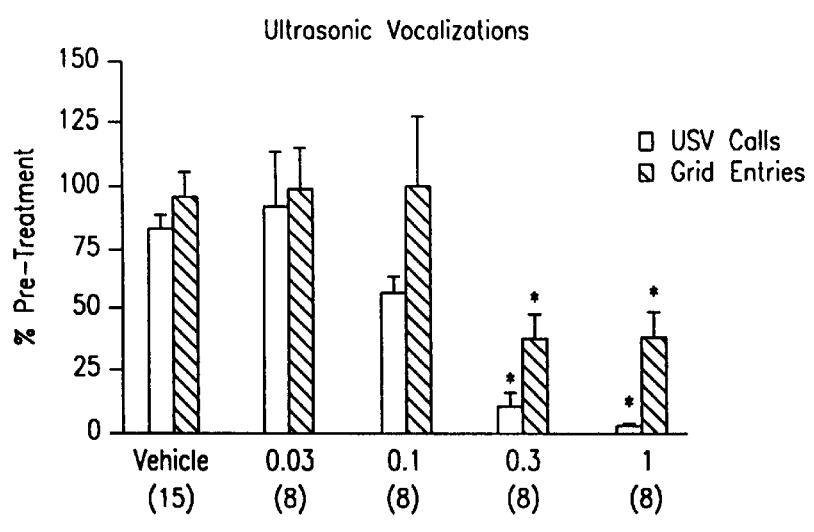
FIG. 2. Effect of buspirone on isolation-induced ultrasonic vocalization and locomotor activity in the rat pup.

Ultrasonic vocalizations emitted by rat pups following isolation from their mother and littermates and subjected to a variety of environmental stimuli (e.g., cold temperature) has proven to be a sensitive method for assessing potential anxiolytic and anxiogenic compounds (Winslow and Insel, 1991, *Psychopharmacology*, 105:513–520). Psychoactive compounds purported to be anxiolytic suppress the frequency of ultrasonic calls whereas, calls are increased by drugs with anxiogenic properties. More importantly, the isolation-induced ultrasonic vocalization paradigm appears to be most sensitive for detecting anxiolytic properties across a broad spectrum of drug classes such as benzodiazepines, 5-HT reuptake inhibitors, 5-HT1A agonists as well as NMDA antagonists. In the present investigation, the 6-hydroxylated metabolite of buspirone, BMY 28674, which has affinity for the human 5-HT1A receptor ($K_i$=57 nM) was assessed for potential anxiolytic activity using 9–11 day old rat pups that had been separated from their mother and littermates and placed on a cold (18–20° C.) plate to elicit distress-induced ultrasonic vocalizations. See FIG. 1. FIG. 2 shows the results obtained for buspirone in this test method.

Administration of BMY 28674 (0.03–1 mg/kg, sc; FIG. 1) 30 min prior to test produced a dose-dependent suppression of rat pup ultrasonic vocalization on the cold plate [$F(4, 45)=19.27, p=0.0001$]. The dose of BMY 28674 predicted to reduce the number of calls by 50% ($ID_{50}$) was 0.13 mg/kg. Locomotor activity was also significantly impaired following BMY 28674 [$F(4,45)=5.85, p=0.007$]. However, the $ID_{50}$ dose (0.41 mg/kg) of BMY 28674 estimated to reduce locomotor activity was approximately 3-fold greater than the $ID_{50}$ dose (0.13 mg/kg) observed for suppressing ultrasonic calls suggesting that like buspirone, the anxiolytic properties of BMY 28674 occurs at lower doses.

Administration of buspirone (0.03–1 mg/kg, sc; FIG. 2) 30 min prior to test produced a dose-dependent suppression of rat pup ultrasonic vocalization on the cold plate [$F(4, 42)=15.44, p=0.0001$]. The dose of buspirone predicted to reduce the number of calls by 50% ($ID_{50}$) was 0.10 mg/kg. Locomotor activity was also impaired [$F(4,42)=4.343, p=0.005$] at approximately 5-fold greater doses than those suppressing ultrasonic calls.

The present results demonstrate that, like buspirone, the metabolite BMY 28674 elicits anxiolytic-like activity in the rat pup isolation-induced ultrasonic vocalization model of anxiety. The anxiolytic activity associated with BMY 28674 (and buspirone) occurred at much lower doses than those required to suppress motor activity. In summary, the foregoing in vitro and in vivo tests demonstrate positive antianxiety test results for both buspirone and BMY 28674; however, buspirone blood level concentrations are minute following oral administration to human subjects. Prior to the present work, no information regarding clinical blood level concentrations of BMY 28674 existed.

Human pharmacokinetic studies have been undertaken and have yielded surprising results further supporting the role of BMY 28674 as the active anxiolytic metabolite.

Human subjects (n=13) were administered buspirone orally for 25 days with total daily doses ranging from 10 mg to 60 mg. The dosing schedule was divided into five 5-day dose intervals with BID dosing being increased in each interval. Pharmacokinetic measurements were made on day 5 of each interval and these data were used to assess the pharmacokinetics of buspirone, 1-PP, and BMY 28674. The human dosing schedule is shown below.

| Dosing Interval | Buspirone BID Dose (mg) | PK Measurement (Study Day) |
| --- | --- | --- |
| 1 | 5 | 5 |
| 2 | 7.5 | 10 |
| 3 | 15 | 15 |
| 4 | 20 | 20 |
| 5 | 30 | 25 |

These multiple doses of oral buspirone at the five dose levels were found to be safe and generally well tolerated in the healthy adults participating in the 25-day study.

Figure 3:
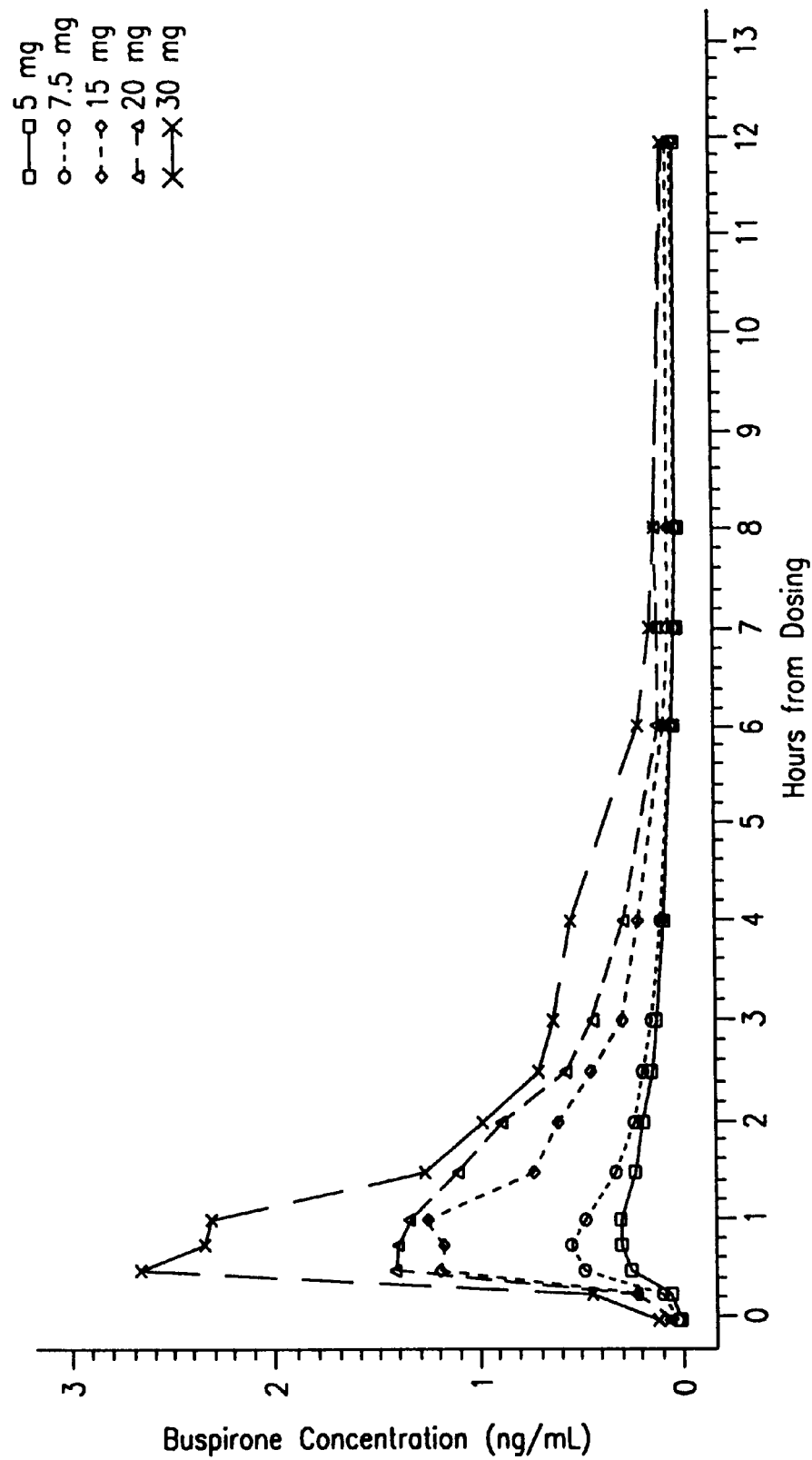
FIG. 3. Human blood level concentrations of buspirone following oral dosing of buspirone in human subjects.
Figure 4:
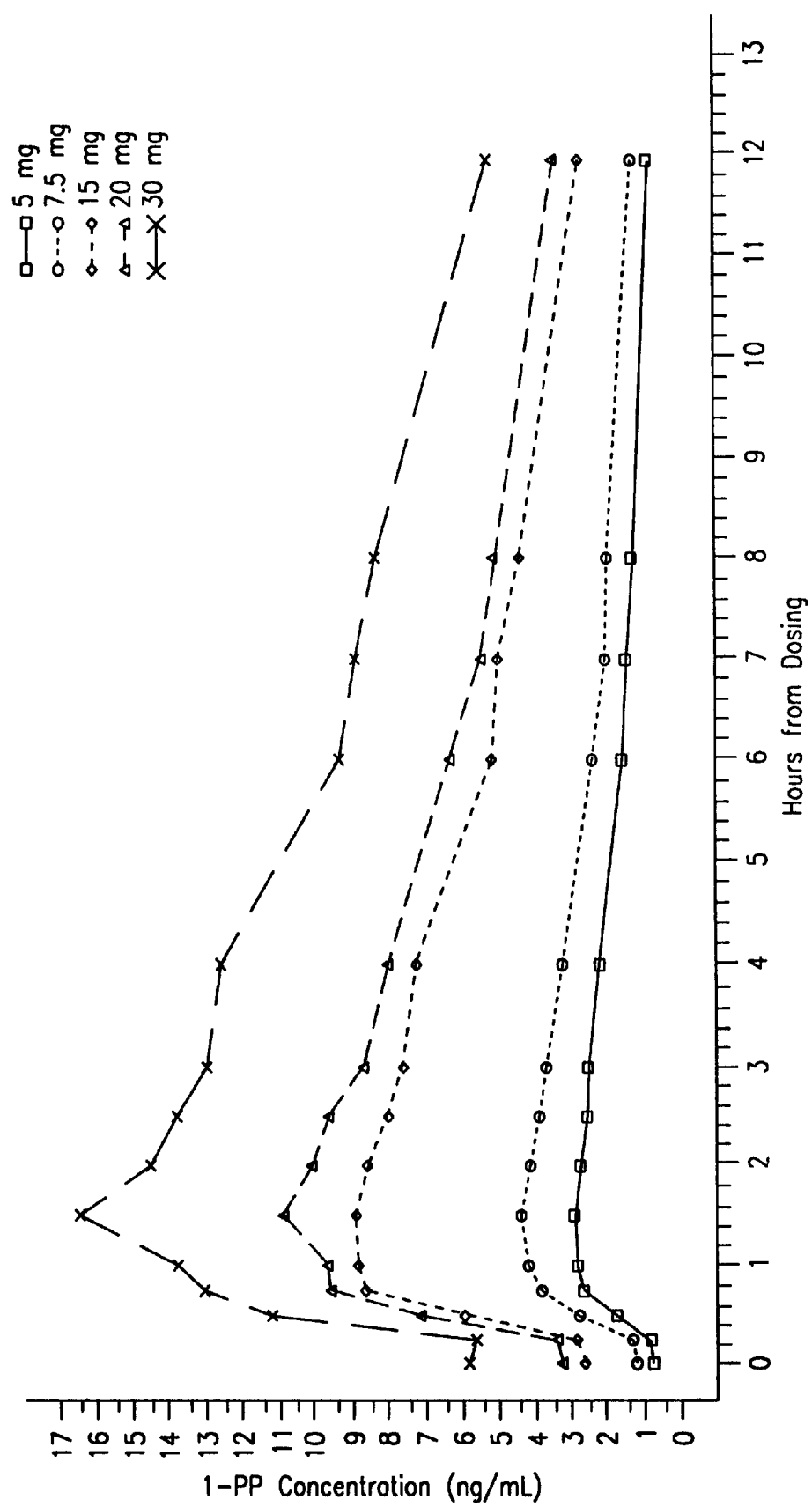
FIG. 4. Human blood level concentrations of 1-PP following oral dosing of buspirone in human subjects.
Figure 5:
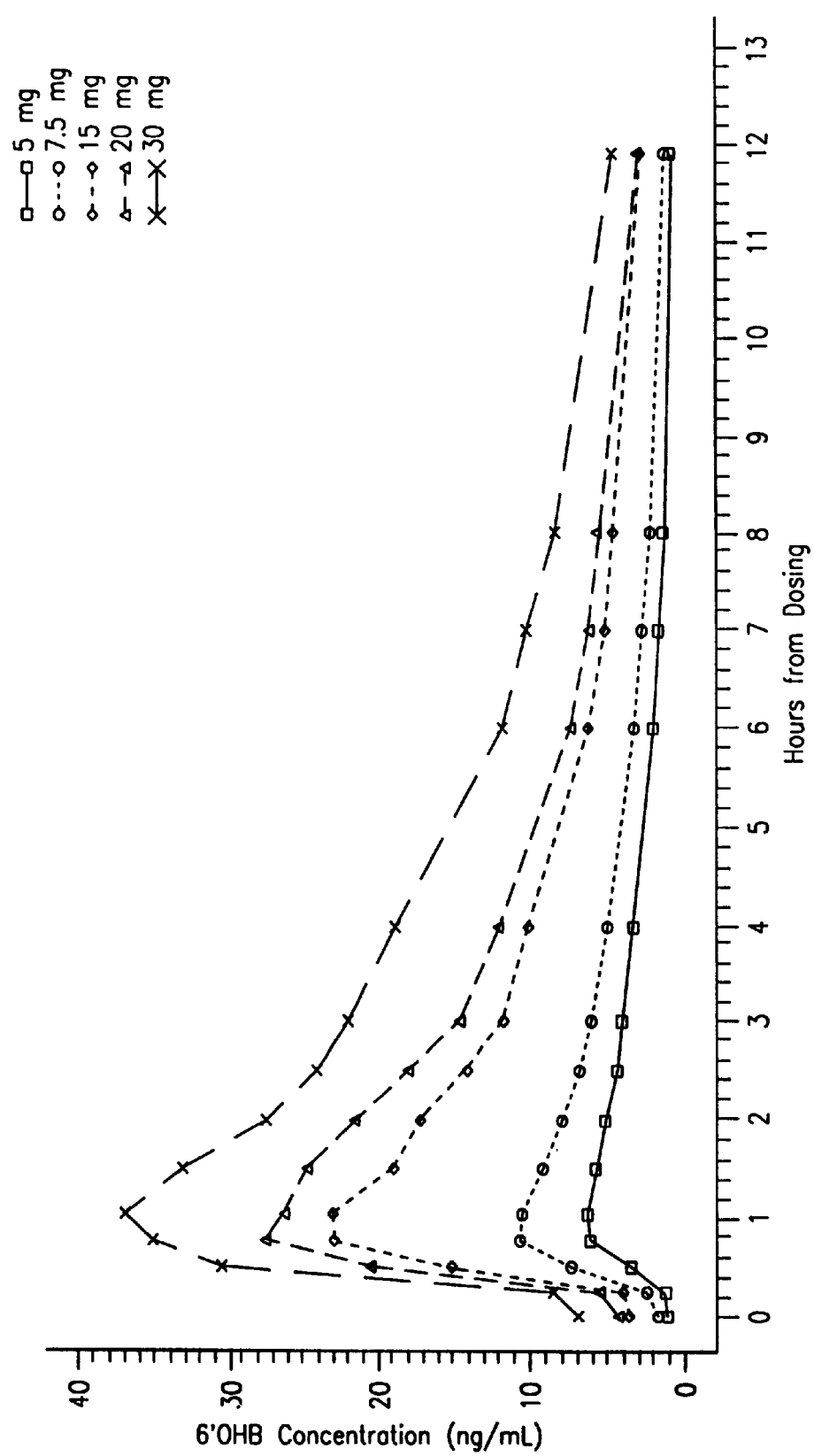
FIG. 5. Human blood level concentrations of BMY 28674 following oral dosing of buspirone in human subjects.

FIGS. 3, 4 and 5 show mean blood level concentrations of buspirone, 1-PP, and BMY 28674, respectively, over a 12-hour dosing period on the last day of each dosing interval. Buspirone levels (FIG. 3) are in general very low (about 1–2 ng/mL at the higher doses) and drop to less than 1 ng/mL levels two hours post-dose. In contrast, 1-PP levels (FIG. 4) and BMY 28674 levels (FIG. 5) are much higher and are sustained compared to buspirone. BMY 28674 has several-fold higher concentrations than 1-PP and about 30 to 40-fold higher concentrations than buspirone.

Thus far, studies indicate that after oral administration of buspirone, it is blood levels of the metabolite, BMY 28674, that are meaningful compared to the negligible blood levels of buspirone that are seen. Although buspirone itself has been demonstrated to have anxiolytic properties in test models such as the rat pup USV model described herein, the low blood level concentrations seen in humans leads to the conclusion that it is the abundant metabolite BMY 28674 that mediates the antianxiety effect seen clinically. Prior to this present evaluation of buspirone metabolites, the relative abundance of BMY 28674 in humans following oral administration of buspirone was not known.

While it is evident that BMY 28674 can itself be administered to achieve an anxiolytic effect, oral administration of its precursor, buspirone, done under appropriate conditions can also offer an improved method of introducing BMY 28674 into the system of an anxious patient. To gain better definition of these conditions, in vitro metabolism experiments were performed to study the Human Liver Microsomal (HLM) metabolism of buspirone. Multiple donor preparations of HLM were chosen based upon their CYP3A4 enzyme activities. HLM preparations were purchased from Gentest Corporation (Woburn, MA: Catalog #'s, H023, H056, H070, H093 and H112), who characterized the HLM preparations utilizing standard procedures. In addition to measuring the loss of parent compound in the incubations, the metabolite, BMY 28674, levels were also measured.

Figure 6:
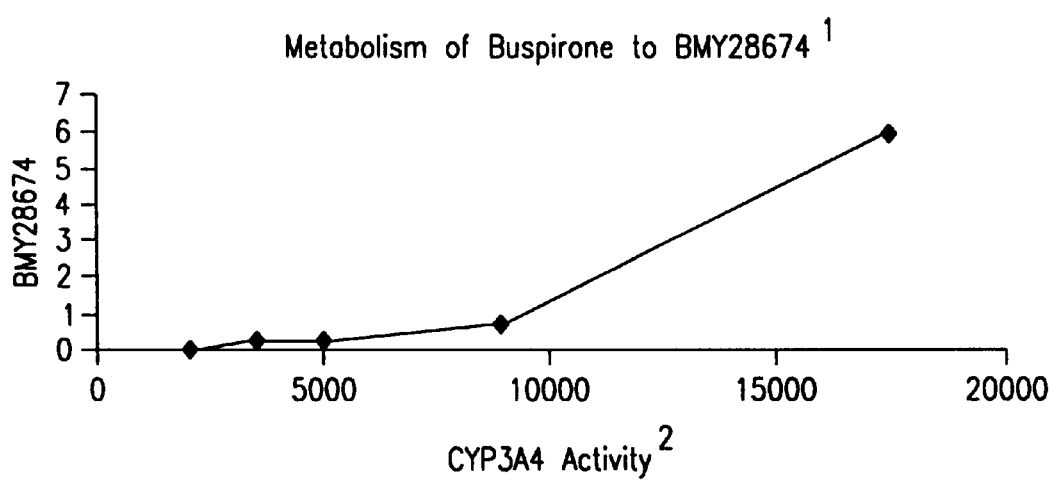
FIG. 6. In Vitro metabolism study: Human Liver Microsomal (HLM) metabolism of buspirone to produce BMY 28674.

The first set of experiments measured the correlation seen in FIG. 6 between the specific activity of CYP3A4 in HLM preparations and the metabolism of buspirone and the production of the metabolite. A single concentration of $^{14}$C-buspirone (10 μM) was incubated with five HLM preparations from five donor livers. Incubations were performed for 15 minutes with 0.5 mg/ml microsomal protein and utilized an NADPH generating system. $^{14}$C-buspirone and BMY 28674 levels in the incubation samples were determined by reverse-phase HPLC, utilizing online radioactivity detection and comparison to authentic standards. Quantitative recovery of $^{14}$C was obtained. The ratio of BMY 28674 to buspirone concentration versus CYP3A4 specific activity as measured in HLM preparations from five donor livers is shown in FIG. 6 (mean of two separate determinations). These results show that the ratio of BMY 28674 to buspirone increases as the CYP3A4 specific activity increases in HLM. The change in ratio as CYP3A4 activity increases is noted by both an increase in BMY 28674 levels, and a decrease in buspirone concentrations (results not shown).

A second set of incubations was performed to determine the potential of a CYP3A4 inhibitor to alter the ratio of BMY 28674 to buspirone in HLM incubations. A single concentration of $^{14}$C-buspirone (10 μM) was incubated with pooled HLM (pooled by combining equal volumes from the five donor livers described above). Ketoconazole, a well-characterized CYP3A4 inhibitor, was added to the incubations at various concentrations. All other incubation conditions, as well as the analysis of the samples, was as described above. In the absence of ketoconazole, following the 15-minute incubation of buspirone with the pooled HLM, the ratio of BMY 28674 to buspirone was 0.42 (Table 2). No effect on buspirone metabolism was noted at ketoconazole concentrations up to 0.125 μM. At 0.25 μM ketoconazole, the ratio of 6'-hydroxy-buspirone to buspirone decreased to 0.32. At the higher ketoconazole concentrations of 1.25 μM and 2.5 μM, the ratio of BMY 28674 to buspirone decreased further to 0.06 and 0.01, respectively. These results show that when ketoconazole is co-incubated with buspirone in pooled HLM, the ratio of BMY 28674 to buspirone decreases as the concentration of the CYP3A4 inhibitor ketoconazole increases. The change in ratio as ketoconazole concentration increases is noted by both a decrease in BMY 28674 levels and an increase in unchanged buspirone concentrations.

TABLE 2

Inhibition of the Metabolism of Buspirone by Ketoconazole

| [ketoconazole] (uM) | [buspirone] (Relative CPM) | [BMY 28674] | [BMY 28674/ buspirone] (Ratio) |
|---|---|---|---|
| 0 | 20054 | 8400 | 0.42 |
| 0.025 | 18645 | 7884 | 0.42 |
| 0.125 | 19648 | 8201 | 0.42 |
| 0.25 | 21957 | 7052 | 0.32 |
| 1.25 | 36117 | 2111 | 0.06 |
| 2.5 | 43712 | 576 | 0.01 |

In summary, these in vitro experiments show the dependence of both the metabolism of buspirone and the appearance of the metabolite BMY 28674 on the CYP3A4 activity in human liver.

It is an objective of this invention to provide an improved method of eliciting an anxiolytic response in anxious patients. This objective is met by providing anxiolytic-effective blood levels of BMY 28674 in anxious patients. The most apparent means to achieve this would be by systemic administration of BMY 28674 itself to the patient. Therefore, one aspect of the present invention concerns the process for ameliorating an anxiety state in a mammal in need of such treatment by systemic administration of an effective antianxiety dose of BMY 28674.

An effective dose should, in general, provide minimum blood level concentrations (CMIN) of BMY 28674 that are at least 1 to 2 ng/mL. Generally the point of measurement for CMIN levels is 12 hours post-dose; i.e., just before the next BID dose. BMY 28674 can be administered by a variety of routes including, but not limited to, oral; sublingual; buccal; transnasal; or parenteral, e.g. intramuscular, intravenous, subcutaneous, etc.

Therapeutically, BMY 28674 can be given by one of these routes as a formulation comprised of an effective anxiolytic amount of BMY 28674, or one of its pharmaceutically acceptable acid addition salts or a hydrate, in a pharmaceutically acceptable carrier. Pharmaceutical compositions which provide from about 5 to 50 mg of the active ingredient per unit dose are preferred and can be conventionally prepared as aqueous solutions and aqueous or oily suspensions. BMY 28674 can also be given orally when compounded in an oral dosing formulation such as a tablet, lozenge, capsule, syrup, elixir, aqueous solution or suspension.

The pharmaceutically acceptable acid addition salts of BMY 28674 are also considered useful as anxiolytic agents. By definition, these are those salts in which the anion does not contribute significantly to toxicity or pharmacological activity of the base form of BMY 28674.

Acid addition salts are obtained either by reaction of BMY 28674 with an organic or inorganic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, and the like; useful inorganic acids are hydrohalide acids such as HCl, HBr, HI; sulfuric acid; phosphoric acid; and the like.

Preferred oral compositions are in the form of tablets or capsules and in addition to BMY 28674 may contain conventional excipients such as binding agents (e.g., syrup, acacia, gelatin, sorbitol, tragecanth, or polyvinyl pyrrolidone), fillers (e.g., lactose, sugar, maize-starch, calcium phosphate, sorbitol or glycine), lubricants (e.g., magnesium stearate, talc, polyethyleneglycol or silica), disintegrants (e.g., starch), and wetting agents (e.g., sodium lauryl sulfate). Solutions or suspensions of BMY 28674 with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active ingredient (BMY 28674 or a pharmaceutically acceptable acid addition salt or hydrate thereof) in water or a vehicle consisting of a polyhydric aliphatic alcohol such as glycerine, propylene glycol, and polyethylene glycols or mixtures thereof. The polyethylene glycols consist of a mixture of non-volatile, normally liquid, polyethylene glycols which are soluble in both water and organic liquids and which have molecular weights from about 200 to 1500.

BMY 28674 may be synthesized by methods readily available in the chemical literature and known to one skilled in synthetic organic chemistry. One method of preparation utilizes buspirone as a starting material and the process is shown in Scheme 2.

in dosage amounts that would produce effective anxiolytic effects without causing harmful or untoward side-effects. That is, systemic administration of BMY 28674 may be accomplished by oral administration of a precursor or prodrug form of BMY 28674, e.g. buspirone, to mammals.

However, this method of systemic introduction of BMY 28674 improves upon and differs from the known standard method of oral administration of buspirone. The prodrug buspirone is utilized in an improved method of effecting anxiolysis in the present invention. Thus, another aspect of this invention is directed to ameliorating anxiety in a mammal by an improved method of oral administration of buspirone. The improvement involves the oral administration of buspirone in such a manner that the metabolic production of BMY 28674 is favored, thereby providing anxiolytic-effective amounts of BMY 28674 in the patient. This is in contradiction to currently accepted methods of administration that are directed to maximizing blood levels of unchanged buspirone. As an example, dosing guidance in the past has taught that if buspirone is administered under conditions favoring inhibition of its metabolism, i.e. where higher levels of unchanged buspirone and lower levels of metabolite will result, the dose of buspirone should be

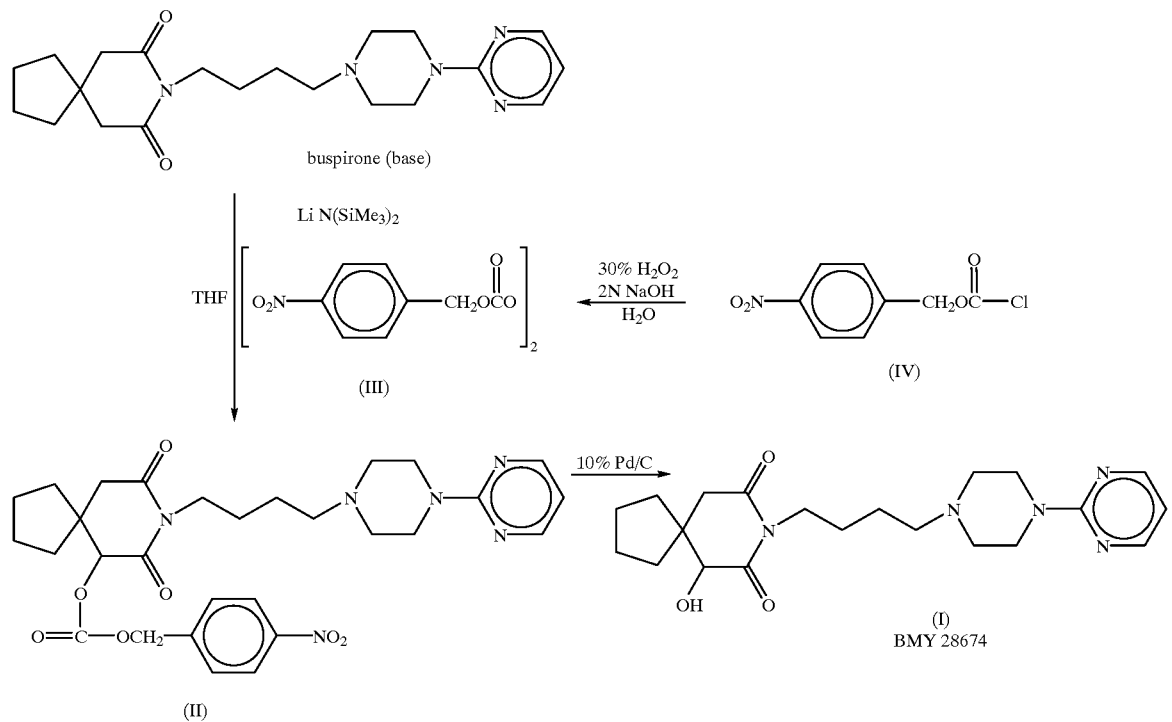

Scheme 2
Preparation of BMY 28674

This method of preparation is provided as a helpful example and illustrates a convenient synthesis of BMY 28674.

It should also be appreciated that BMY 28674 can be obtained by enzymatic (human or rat liver microsomes) conversion of buspirone in vitro. (See: Jajoo, et al., *Xenobiotica*, 1990, Vol. 20, No. 8, pp. 779–786.)

Systemic administration may also be realized by a second method of achieving effective anxiolytic blood levels of BMY 28674 which is to orally administer a precursor form of BMY 28674. Such prodrug forms would be administered reduced. The improved method is directly counter to the past method of orally administering buspirone. Instead of reducing the dose of buspirone when its metabolism is inhibited, the dose of buspirone should be increased in order to achieve appropriate levels of BMY 28674. There has been no specific correlation of serious adverse effects to increased amounts of buspirone being ingested.

In summary, the second aspect of the current invention concerns an improved process of ameliorating an undesirable anxiety state in a mammal by oral administration of buspirone, or a pharmaceutically acceptable acid addition salt thereof, in a manner favoring metabolic production of BMY 28674 in the mammal. In general, the amount of buspirone to be given is a dose that results in a minimum blood concentration (CMIN) of I to 2 ng/mL of BMY 28674. CMIN determinations in patients are usually made 12 hours after a drug dose and just prior to the next dose.

An example of one factor affecting metabolic production of BMY 28674 is the effect of food on oral dosing of buspirone. According to the package insert for BUSPAR® (buspirone HCl oral tablets), the implicit suggestion is made that buspirone be taken with food to increase the plasma concentration of unchanged buspirone.

A second example of a dosing modification taught in the BUSPAR® package insert is the recommendation of lowering the buspirone dosage when given in combination with an inhibitor of CYP3A4.

For purposes of the improved method of ameliorating an undesirable anxiety state by oral administration of buspirone, the foregoing examples teach away from the improved method of the current invention. Instead of dosing buspirone at mealtimes, the dosing should occur about two hours or more before or after a meal. Similarly, in the case of decreased functioning of cytochrome P450 3A4 (CYP3A4), the dose of buspirone should be increased and not decreased, as taught by the BUSPAR® package insert.

Other dosing modifications envisioned for the improved anxiolytic method involving systemic introduction of BMY 28674 by oral administration of buspirone comprise the following.

Administer oral buspirone in coincidence with diurnal periods of maximal CYP3A4 activity in the mammal.

Discontinue concomitant medications or foodstuffs that inhibit CYP3A4 activity.

Increase the dose of buspirone to adjust for decreased CYP3A4 activity when discontinuance of concomitant medication that inhibits the cytochrome activity is medically impractical.

In sum, oral administration of buspirone to an anxious patient is modified in manner and degree, in accordance with good medical practice, so that the metabolic production of BMY 28674 is favored. In keeping with good clinical practice, it is preferable to administer BMY 28674, or a precursor form, at concentration levels that will produce effective anxiolytic effects without causing harmful or untoward side-effects.

Description of Specific Embodiments

The compound whose use constitutes this invention and its method of preparation will appear more fully in light of the following examples which are given for the purpose of illustration only and are not to be construed as limiting the invention in sphere or scope.

EXAMPLE 1

Preparation of BMY 28674 (I)

A. Di-4-nitrobenzyl peroxydicarbonate (III)

Di-4-nitrobenzyl peroxydicarbonate was prepared using a modification of the literature procedure[1]. Thus, to an ice-cold solution of 4-nitrobenzyl chloroformate (10.11 g, 4.7 mmol) in acetone (20 mL) was added dropwise over 30 min an ice-cold mixture of 30% $H_2O_2$ (2.7 mL, 24 mmol) and 2.35 N NaOH (20 mL, 47 mmol). The mixture was vigorously stirred for 15 min and then it was filtered and the filter-cake was washed with water and then with hexane. The resulting damp solid was taken up in dichloromethane, the solution was dried ($Na_2SO_4$) and then it was diluted with an equal volume of hexane. Concentration of this solution at 20° C. on a rotary evaporator gave a crystalline precipitate which was filtered, washed with hexane and dried in vacuo to give compound III (6.82 g, 74%) as pale yellow microcrystals, mp 104° C. (dec).

[1]F. Strain, et al., *J. Am. Chem. Soc.*, 1950, 72, 1254

Di-4-nitrobenzyl peroxydicarbonate was found to be a relatively stable material which decomposed as its melting point with slow gas evolution. In comparison, dibenzyl peroxydicarbonate[2] decomposed with a sudden vigorous expulsion of material from the melting point capillary.

[2]Cf. M. P. Gore, J. C. Vederas, *J. Org. Chem.*, 1986, 51, 3700

B. 6-(4-Nitrobenzyl peroxydicarbonatyl)-8-[4-[4-(2-pyrimidinyl)-piperazinyl]-butyl]-8-azaspiro[4.5]-7,9-dione (II)

To a solution of 8-[4-[4-(2-pyrimidinyl)-piperazinyl]-8-azaspiro[4.5]-7,9-dione (buspirone: 10 g, 26 mmole) in dry THF (250 mL) was added LiN $(Me_3Si)_2$ (28.5 mL of a 1 M THF solution) at −78° C. and stirred for 3 h and then a solution of di4-nitrobenzyl peroxydicarbonate (11.2 g) in dry THF (150 mL) was added dropwise over 1 h. Stirring was continued at −78° C. for 1 h.

The cooling bath was removed and the reaction solution was poured into a mixture of $H_2O$ and EtOAc. The organic phase was separated and washed with $H_2O$ and then brine. The organic base was dried and then evaporated to a viscous oil. Flash chromatography of this oil, eluting the silica column with MeCN-EtOAc (1:2) gave crude product which was washed with acetone, to remove unreacted buspirone, leaving 6.23 g of a white solid (46%) product (II).

C. 6-Hydroxy-8-[4-[4-(2-pyrimidinyl)-piperazinyl]-butyl]-8-azaspiro[4.5]-7,9-dione (I; BMY 28674)

A mixture of II (4.0 g; 6.9 mmole) and 10% Pd/C (about 1 g) in MeOH (100 mL) was hydrogenated in a Parr shaker at 40–45 psi for 1 h. The hydrogenation mixture was filtered through a Celite pad which was then washed with EtOAc. The filtrate was evaporated to a gum which was purified by flash chromatography through a silica gel column eluting with EtOAc to give 0.41 g of an off-white solid (I).

Anal. Calcd. for $C_{21}H_{31}N_5O_3$: C, 62.82; H, 7.78; N, 17.44. Found: C, 62.84; H, 7.81; N, 17.33.

EXAMPLE 2

5-HT1A Receptor Binding Assay

Membranes are prepared for binding using the human 5-HT1A receptor expressed in HEK293 cells. Cells are collected and ruptured using a dounce homogenizer. The cells are spun at 18000×g for 10 minutes and the pellet is resuspended in assay buffer, frozen in liquid nitrogen and kept at −80° C. until the day of the assay.

A total of 30 ug protein is used per well. The assay is carried out in 96-deep-well plates. The assay buffer is 50 mM HEPES containing 2.5 mM $MgCl_2$ and 2 mM EGTA. The membrane preparation is incubated at 25° C. for 60 minutes with 0.1 nM to 1000 nM test compound and 1 nM 3H-8-OH-DPAT. 10 mM serotonin serves as blocking agent to determine non-specific binding. The reaction is terminated by the addition of 1 ml of ice cold 50 mM HEPES buffer and rapid filtration through a Brandel Cell Harvester using Whatman GF/B filters. The filter pads are counted in an LKB Trilux liquid scintillation counter. $IC_{50}$ values are determined using non-linear regression by Excel-fit.

EXAMPLE 3

Rat Pup Isolation-Induced Ultrasonic Vocalization Test

Harlan Sprague-Dawley rat pups (male and female) were housed in polycarbonate cages with the dam until 9–11 days old. Thirty minutes before testing, pups were removed from the dam, placed into a new cage with a small amount of home bedding and brought into the lab and placed under a light to maintain body temperature at 37° C. Pups were then weighed, sexed, marked and returned to the litter group until behavioral assessment. Testing took place in a Plexiglas recording chamber that contained a metal plate maintained at (18–20° C.) with a 5×5 cm grid drawn on the plate. A microphone was suspended 10 cm above the plate to record ultrasonic vocalizations. Ultrasonic calls were recorded using the Noldus UltraVox system providing on-line analysis of the frequency and duration of calls. The number of grid cells entered by the pup was also collected by visual scoring. Pups that failed to emit at least 60 calls during a 5-minute pretest session were excluded from pharmacological assessment. Immediately following the collection of the baseline measures, pups were injected with vehicle or drug subcutaneously at the nape of the neck and returned to its littermates. Thirty minutes later, pups were retested on each of the dependent measures (vocalization and grid cell crossings) to assess drug effects. Unless otherwise specified, each pup was used only once. Baseline differences and percent change from baseline for the frequency of ultrasonic vocalizations and grid cell crossings were analyzed using a one-way ANOVA. Bonferroni/Dunn post hoc comparisons were performed to assess the acute drug effects with vehicle control. Log-probit analysis was used to estimate the dose (milligrams per kilogram) of each agonist predicted to inhibit isolation-induced ultrasonic vocalizations by 50% ($ID_{50}$). All comparison were made with an experimental type I error rate ($\alpha$) set at 0.05.

Doses for each drug were administered in an irregular order across several litters. BMY 28674 and buspirone were dissolved in physiological saline (0.9% NaCl; vehicle). All injections were administered subcutaneously in a volume of 10 ml/kg. Doses of the drugs refer to the weight of the salt.

EXAMPLE 4

In Vitro Metabolism Studies: Buspirone Conversion to BMY 28674

5 donor preparations of HLM were chosen based upon their CYP3A4 Cytochrome P450 enzyme activities.

$^{14}$C-buspirone (10 $\mu$M) was incubated with five HLM preparations from five donor livers (15 minutes with 0.5 mg/ml microsomal protein).

$^{14}$C-buspirone and BMY 28674 levels in the incubation samples were determined by reverse-phase HPLC, utilizing on-line radioactivity detection and comparison to authentic standards.

A second set of incubations was performed to determine the potential of ketoconazole (a CYP3A4 inhibitor) to alter the ratio of BMY 28674 to BUSPAR® in HLM incubations.

$^{14}$C-buspirone (10 $\mu$M) was incubated with pooled HLM (15 minutes with 0.5 mg/ml microsomal protein).

What is claimed is:

1. A process for ameliorating an undesirable anxiety state in a mammal comprising systemic administration to the mammal of an effective but non-toxic anxiolytic dose of 6-hydroxy-8-[4-[4-(2-pyrimidinyl)-piperazinyl]-butyl]-8-azaspiro[4.5]-7,9-dione or a pharmaceutically acceptable acid addition salt or hydrate thereof.

* * * * *